(12) United States Patent
Derks et al.

(10) Patent No.: US 6,838,515 B2
(45) Date of Patent: Jan. 4, 2005

(54) PROCESS FOR THE PREPARATION OF ESTERS OF (METH)ACRYLIC ACID

(75) Inventors: Franciscus J.M. Derks, Heythuysen (NL); Michael A.C. Van Dijck, Elsloo (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/042,286

(22) Filed: Jan. 11, 2002

(65) Prior Publication Data

US 2002/0156317 A1 Oct. 24, 2002

Related U.S. Application Data

(60) Provisional application No. 60/265,308, filed on Feb. 1, 2001, and provisional application No. 60/260,672, filed on Jan. 11, 2001.

(51) Int. Cl.$^7$ .................. C08G 63/46; C08G 63/91; C07C 67/60
(52) U.S. Cl. .............. 525/48; 525/7; 525/10; 528/303; 560/205; 560/218
(58) Field of Search ............... 525/7, 10, 48, 525/920, 921; 528/303; 560/205, 218

(56) References Cited

U.S. PATENT DOCUMENTS

| | | | |
|---|---|---|---|
| 4,130,518 A | | 12/1978 | Rybny et al. |
| 4,420,416 A | * | 12/1983 | Larsen ............... 502/168 |
| 5,516,860 A | * | 5/1996 | Reich ................ 525/531 |

FOREIGN PATENT DOCUMENTS

| | | |
|---|---|---|
| BE | 814979 | 11/1974 |
| BE | 846356 | 3/1977 |
| DE | 2731085 | 1/1978 |
| DE | 2638867 | 3/1978 |
| DE | 2639667 | 3/1978 |
| DE | 2641662 | 3/1978 |
| DE | 2838691 | 3/1979 |
| DE | 3214264 | 5/1984 |
| DE | 3316593 | 11/1984 |
| DE | 3319013 | 11/1984 |
| DE | 3836370 | 5/1990 |
| DE | 4040290 | 7/1992 |
| DE | 4126860 | 2/1993 |
| DE | 196 02 071 | 6/1996 |
| DE | 196 00 136 | 7/1997 |
| DE | 196 16 984 | 10/1997 |
| EP | 2866 | 7/1979 |
| EP | 54105 | 6/1982 |
| EP | 87580 | 9/1983 |
| EP | 127766 | 12/1984 |
| EP | 144703 | 6/1985 |
| EP | 279303 | 8/1988 |
| EP | 350730 | 1/1990 |
| EP | 407826 | 1/1991 |
| EP | 624609 | 11/1994 |
| EP | 680985 | 11/1995 |
| EP | 686621 | 12/1995 |
| EP | 739922 | 10/1996 |
| EP | 775687 | 11/1996 |
| EP | 874014 | 4/1998 |
| EP | 900778 | 8/1998 |
| EP | 933353 | 1/1999 |
| NL | 7707669 | 7/1977 |
| WO | 97/46594 | 12/1997 |
| WO | 98/14500 | 4/1998 |
| WO | 98/18862 | 5/1998 |
| WO | 98/18874 | 5/1998 |
| WO | 98/56500 | 12/1998 |
| WO | 99/21894 | 5/1999 |

* cited by examiner

Primary Examiner—Jeffrey B. Robertson
(74) Attorney, Agent, or Firm—Mayer, Brown, Rowe & Maw LLP

(57) ABSTRACT

The invention relates to a process for the preparation of esters of (meth)acrylic acid by (trans)esterifying (meth)acrylic acid or its ester derivatives with monohydric or polyhydric alcohols in the presence of an acidic (trans)esterification catalyst, wherein said process after the formation of the esters of (meth)acrylic acid further comprises reacting remaining acid groups with one or more component(s), wherein at least one component forms with at least said catalyst an ester compound not having a β-hydroxy group or forms an amid compound. The component that reacts with the acidic (trans)esterification catalyst preferably is selected from the group consisting of an oxetane component or derivative, an ortho-ester component, an alcohol component or any mixture thereof.

21 Claims, No Drawings

PROCESS FOR THE PREPARATION OF ESTERS OF (METH)ACRYLIC ACID

This application claims the benefit of U.S. Provisional Application Nos. 60/260,672, filed Jan. 11, 2001 and 60/265,308 filed Feb. 1, 2001. Both of the provisional applications are hereby incorporated in their entirety by reference.

FIELD OF THE INVENTION

The present invention relates to a process for the preparation of esters of (meth)acrylic acid in the presence of an acidic (trans)esterification catalyst and to a process for neutralizing an acidic (trans)esterification catalyst. With (trans)esterification is meant both esterification as well as trans-esterification.

BACKGROUND OF THE INVENTION

It is known from DE-2838691 (UCB) to prepare acrylic polyesters by reacting hydroxy-functional polyesters with acrylic acid and by removing remaining acid(s) by an aqueous base neutralization step.

The process as described in DE-2838691 has the disadvantage that a complicated and time-consuming washing step, including different separation steps, is used to remove acidic catalyst and remaining acrylic acid. Moreover, said washing step results in chemical waste, and is thus environmentally unfriendly.

It is an object of the present invention to provide a process for the preparation of esters of (meth)acrylic acid in the presence of an acidic (trans)esterification catalyst which overcomes the above disadvantage, in particular, a process which avoids the necessity of a complicated washing step to remove free acid groups of the acidic catalyst.

It is a further object of the present invention to provide a process for neutralizing an acidic (trans)esterification catalyst in a reaction mixture comprising an ester compound without the necessity for said washing step.

SUMMARY OF THE INVENTION

Surprisingly, one or more of the above objects are obtained by a process for the preparation of esters of (meth)acrylic acid by (trans)esterifying (meth)acrylic acid or its ester derivatives with monohydric or polyhydric alcohols in the presence of an acidic (trans)esterification catalyst, wherein said process after the formation of the esters of (meth)acrylic acid further comprises reacting remaining acid groups with one or more component(s), wherein at least one component forms with at least said acidic catalyst an ester compound not having a β-hydroxy group or forms an amid compound.

The term "monohydric or polyhydric alcohols" refers to all types of monoalcohols and polyalcohols, including as well hydroxy-functional polymers such as for example hydroxy-functional polyesters. This will be elucidated further below.

For comparison, an ester compound having a β-hydroxy group is represented by the following formula (1):

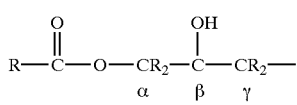

(1)

With the term (meth)acrylic acid is meant a compound according to the following formula (2):

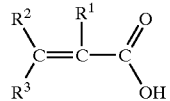

(2)

wherein: $R^1$, $R^2$, $R^3$ can be the same or different and are chosen from hydrogen, C1–C12 alkyl or alkaryl, C6–C12 aryl or arylalkyl or halogen, or —$CH_2$—X, wherein X can be chosen from the list: halogen, hydroxy or alkoxy with 1–6 carbon atoms. For example when $R^1$, $R^2$ and $R^3$ are all hydrogen the compound is acrylic acid, when $R^1$ and $R^2$ are hydrogen and $R^3$ is methyl, the compound is crotonic acid, when $R^2$ and $R^3$ are hydrogen and $R^1$ is methyl, the compound is methacrylic acid, when $R^1$ and $R^2$ are hydrogen and $R^3$ is phenyl, the compound is cinnamic acid.

According to a further embodiment of the present invention, one or more of the above objects are obtained by a process for neutralizing an acidic (trans)esterification catalyst in a reaction mixture comprising an ester compound, the process comprising reacting one or more component(s) to said reaction mixture comprising the acidic catalyst, wherein at least one component forms with at least said acidic (trans)esterification catalyst an ester compound not having a β-hydroxy group or forms an amid compound.

The process of the present invention has the additional advantage(s) that esters of (meth)acrylic acid having good hydrolytic stability are obtained and that resins, containing said esters of (meth)acrylic acid, can be obtained that are hydrolytically stable and do not turn turbid over time.

It is further known from EP 0 54 105 A1 (Vianova) to use epoxides to neutralize free acrylic acid that remains after the synthesis of an acrylic polyester. The so-neutralized acrylic polyester does not show good hydrolysis resistance.

It is further known from EP 0 933 353 A1 (BASF) to wash out the catalyst and to remove free acids and alcohols by adding water soluble flocculators to the (poly)esteracrylate reaction mixture. A disadvantage of this process is the necessity of washing, which generates chemical waste and is time-consuming and (therefore) expensive.

DETAILED DESCRIPTION OF THE INVENTION

The improvement found by the present inventors is applicable in any process for the preparation of esters of (meth) acrylic acid by (trans)esterifying (meth)acrylic acid or its ester derivatives with monohydric or polyhydric alcohols in the presence of an acidic (trans)esterification catalyst.

An ester of (meth)acrylic acid can be defined as a (meth) acrylate functional compound being derived from the reaction of an hydroxyl functional compound (i) with (meth) acrylic acid or its ester derivatives (ii), wherein the hydroxyl functional compound can be mono-, di-, or polyfunctional and has as a backbone a R-group. R can contain an aliphatic, cycloaliphatic or aromatic chain, a (poly)ether, (poly)ester for example (poly)caprolactone, (poly)alkyd, (poly) urethane, (poly)amine, (poly)amide, (poly)carbonate, (poly) olefin, (poly)siloxane, (poly)acrylate, halogen (e.g. fluorine), a melamine-derivative, copolymers of any of them, and the like.

A (poly)alkyd is regarded as a type of polyester. An alkyd (meth)acrylate comprises an alkyd backbone derived from an alkyd resin and (meth)acrylate reactive end groups. Alkyd resins, or alkyds, are polyesters having a pendent ester group protruding off of a main polymer chain of ester linkages. The pendent group of the alkyd can be introduced by introducing a monofunctional carboxylic acid (monoacid) along with the suitable components used to prepare the polyester.

For the sake of simplicity, the term "polyester" is further used to refer to both (poly)ester and (poly)alkyd. The term "(meth)acrylate" is used to refer to methacrylate and acrylate.

The ester of (meth)acrylic acid can be prepared by (trans) esterifying (meth)acrylic acid or its ester derivatives (ii) with monohydric or polyhydric alcohols (i) in the presence of an acidic (trans)esterification catalyst.

The (meth)acrylic acid reacts with an hydroxy group bonded to an R-chain, oligomer or polymer, under the formation of a (meth)acrylate ester and a molecule of water. This equilibrium reaction is acid catalyzed. By removal of the reaction water and by use of an excess of (meth)acrylic acid, the equilibrium can be shifted to the reaction product. Mostly, an organic solvent is used to azeotropically aid the removal of the reaction water. This can be followed by vacuum distillation of the solvent. Subsequently the desired ester compound is obtained in high yield.

The synthesis can be carried out in a one-step, a two- or more-step process. In the one-step process, the alcohol compound (i), (meth)acrylic acid or its ester derivatives (ii) and the catalyst are all charged in a reactor in air. In the two-step process, the alcohol component (i) is prepared in a first step and then, the alcohol is further (meth)acrylated in a second step. Details of the one-step and two-step processes will be described further below for the preparation of polyester (meth)acrylates.

In the (trans)esterification process, suitable low and high Mw alcohols (i) can be used. According to one preferred embodiment, a low Mw alcohol (i) having 8 or less carbon atoms is used which has the advantage of having a low viscosity. The Mw of said low Mw alcohol is preferably below about 240, more preferred, below about 200.

In a further embodiment, an alcohol (i) is used which has 9 or more carbon atoms, but a Mw of less than 300 being advantageous because of its low viscosity. According to another embodiment, alcohols (i) having a Mw of higher than about 300 and less than about 10,000 are preferred, more preferred, alcohols (i) having a Mw of higher than about 400, even more preferred, higher than about 500. Said alcohols have a high vapor pressure and are therefore less toxic.

As a catalyst, organic acid and inorganic acid catalysts are effective. The catalyst can also have a functional group by which it can be or is, incorporated into a polymer or preferably, into the ester of (meth)acrylic acid e.g. a sulfonic acid functional polymer, a phosphoric acid functional polymer, and the like. Preferably, the catalyst is a strong acid (having a pKa value of about 2 or less, determined at 25° C. in water). As organic acid catalysts, alkyl sulfonic acids such as methane sulfonic acid, aryl sulfonic acids, such as p-toluene sulfonic acid, benzene sulfonic acid, styrene sulfonic acid and the like can be given. As inorganic catalysts, sulfuric acid, the mono-ester of sulfuric acid, phosphoric acid, the mono-ester of phosphoric acid and the like can be given. Catalysts such as p-toluene sulfonic acid are preferred due to their high effectiveness at the relatively low temperatures at which the (meth)acrylation step is carried out.

The concentration of the catalyst in the reaction mixture generally lies between 0.1–10 wt. %, preferably, 0.2–7 wt. %, more preferably, 0.5–5 wt. %, and most preferred, 0.7–3 wt. % (based on the total weight). When polymeric catalysts are used the range 0.1–50 wt % applies, preferably 0.5–40 wt. %, more preferably, 1.0–30 wt. %.

After the esterification (which is optional) and the (meth) acrylation process, some free acid groups can remain in the reaction mixture.

The amount of remaining acid in the ester of (meth) acrylic acid, such as, for example, the remaining (meth) acrylic acid and the remaining acid of the catalyst if applicable (i.e. if used as the catalyst in the (meth)acrylation step during the synthesis of the ester of (meth)acrylic acid) can be quantified by the acid value of the ester of (meth)acrylic acid (further defined as the resin). The acid value of the resin is a measure of the free acids content of a resin and is expressed as the number of milligrams of potassium hydroxide required to neutralize the free acids in one gram of the resin. A weighed quantity of the resin is dissolved in a solvent such as toluene or THF together with neutralized ethyl alcohol and titrated with carbonate-free decinormal potassium hydroxide solution to a phenolphthalein end point. It is also possible to determine the acid value potentiometrically as described further below under test methods section. The acid value can be expressed by formula (3):

$$\text{Acid value} = \frac{(56.1 \times \text{mL KOH} \times \text{normality})}{\text{mass of resin (g)}} (\text{mg KOH/g resin}) \quad (3)$$

After the synthesis of the ester of (meth)acrylic acid, the process of the present invention further comprises a neutralizing step. The "neutralizing" step can be defined as the step in which the acid value of the resin is being reduced. The neutralizing step comprises reacting free acid groups with one or more components wherein at least one component forms with at least said acidic (trans)esterification catalyst an ester compound not having a β-hydroxy group or forms an amid compound.

Said at least one component that reacts with the free acid groups is further referred to as the neutralizing component. The neutralizing system is further defined as comprising said at least one neutralizing component according to the present invention and—optionally—one or more other components (that can react with free acid groups). Said other components can be a β-hydroxy forming component (such as an epoxide), an amine, a carbodiimide component or any mixture thereof.

The neutralizing step can also be catalyzed, if required, by adding a neutralizing catalyst.

Free acid groups can originate from one or more of the following acid groups remaining in the resin after the synthesis step: free catalyst acid, free (meth)acrylic acid groups, and/or free carboxylic acid groups.

According to one embodiment, the neutralizing component reacts with free acid groups originating from the free catalyst acid, free (meth)acrylic acid groups, and free carboxylic acid groups.

According to another preferred embodiment, the neutralizing component according to the present invention reacts predominantly with free catalyst acid.

When more than one component reacts with the free acid groups, the components can all be neutralizing components according to the present invention or the components can consist partly of neutralizing component(s) and partly of said other component(s).

When a β-hydroxy forming component (such as an epoxide), an amine component, a carbodiimide component or any mixture thereof is present (further defined as "the other component(s)"), said other component(s) can be part of the neutralizing system from the beginning or—which is preferred—said other component(s) are added only after the strong catalyst acid has been neutralized with the neutralizing component according to the present invention.

Surprisingly, the ester of (meth)acrylic acid as neutralized according to the process of the present invention is found to be hydrolytically stable and does not turn turbid over time.

The ester or amid compound formed between the catalyst and the neutralizing component as present in the (meth)

acrylic acid ester resin is a hydrolytically stable compound when the resin is stored in an open jar in an oven at 80° C. Preferably, the acid value of the resin does not substantially increase when stored in an open jar in an oven at 80° C. for at least 1 day, preferably, at least 2 days, more preferred, at least 4 days, particularly preferred, at least 1 week, and most preferred, at least 8 weeks.

Said at least one neutralizing component can be selected from the group consisting of cyclic ethers, including 4-membered cyclic ethers such as oxetanes and derivatives, 1,2-dioxetanes, 1,3-dioxetanes; 5-membered cyclic ethers, such as dioxelanes, dihydrofuran, and the like; 6-membered cyclic ethers, such as dioxane and its derivatives, dihydropyran. Other suitable neutralizing components are ortho-esters, esters and lactones, alcohols, carbonates and cyclic carbonates, acetoacetates, chloroformates, chlorosulfites, orthoborates, dialkyl sulfites, urea's, such as N,N'-(bis-2-hydroxyethyl) urea, silyl components, such as bis (trimethylsilyl) sulfate, siloxane components, such as octamethyl cyclo tetrasiloxane, diazo components, such as diazomethane and diazomethyl propylketone, isonitriles, such as phenyl isocyanide, phosphites, such as trialkyl or triaryl phosphites, phosphates, such as trialkyl or triaryl phosphates, phosphonates, such as diethylacetyl phosphonate, tin components, such as dibutyltinoxide. Further suitable neutralizing components are unsaturated components, such as vinyl ethers and cyclic vinyl ethers, allyl ethers, styrenes, olefins and cyclic olefins, maleates, fumarates, acrylates, methacrylates. Other suitable neutralizing components are oxazolines and isocyanates.

Preferred neutralizing components are chosen from the group consisting of a cyclic ether, an ortho-ester, an ester, a lactone, an alcohol, a carbonate, an unsaturated component, or any mixture thereof.

More preferred, the neutralizing component that reacts with the acidic (trans)esterification catalyst is selected from the group consisting of an oxetane component, an ortho-ester component, an alcohol component, or a mixture of two or more thereof. The oxetane and ortho-ester components are preferred because they react relatively fast and quantitatively with the acidic catalyst and therefore, do not require long reaction times or high excess amounts. Ortho-ester components are preferred because they are readily available and relatively cheap. Particularly preferred are the oxetane components, because substantially no side products are formed in the ester formation.

An oxetane component or derivative can be defined by the following formula (4):

(4)

wherein X, Y and Z can be the same or different and can be a $CR_2$-group, a carbonyl (C=O), a heteroatom containing group (preferably, oxygen, nitrogen, —NR, phosphor —PR or P(=O)R), sulfur, or the like. The R groups can be the same or different and can be chosen from the group consisting of hydrogen, methyl, ethyl, propyl, butyl, and the like; halogenated alkyl, such as chloroalkyl (preferably, chloromethyl, chloroethyl), bromoalkyl (preferably, bromomethyl, bromoethyl), fluoroalkyl, and iodoalkyl; hydroxyalkyl, such as hydroxymethyl, and hydroxyethyl, and the like. An oligomeric or polymeric component containing an oxetane moiety (4) can also be suitably used as neutralizing agent in the present invention.

The oxetane component generally has a Mw of at least 58, preferably at least about 70, more preferred, at least about 101, even more preferred, at least about 115, and most preferred, at least about 129. The Mw of the oxetane component is preferably less than about 10,000, more preferably, less than about 8,000.

Suitable examples of an oxetane component (4) are oxetane, 3,3-dimethyl-oxetane, 3-bromoethyl-3-methyl-oxetane, 3-chloroethyl-3-methyl-oxetane, 3,3-dichloroethyl-oxetane, 3-ethyl-3-hydroxymethyl-oxetane, such as Cyracure® UVR6000, 3-methyl-3-hydroxymethyl-oxetane, 1,4-bis(3-ethyl-3-oxetanyl) methoxy, 3-ethyl-3-phenoxymethyl-oxetane, bis{[1-ethyl(3-oxetanyl)]methyl} ether, 3-ethyl-3-[(2-ethylhexyloxy)methyl] oxetane, 3-ethyl-[(tri-ethoxysilylpropoxy)methyl] oxetane, oxetanyl-silsesquioxane, and 3-methyl-3-hydroxymethyl-oxetane acrylate ester, and derivatives thereof, 1,2-dioxetanes, 1,3-dioxetanes, and the like, and mixtures of two or more of the above.

An ortho-ester component or derivative can be defined by the following formula (5):

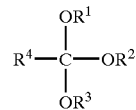

(5)

wherein each of $R^1$ to $R^3$ can be alkyl, cycloalkyl, aryl, and the like, Further, each of $R^1$, $R^2$ or $R^3$ can link to each other to form cycles with each other. $R^4$ can be hydrogen, alkyl, cycloalkyl, aryl, and the like. Alkyl can be methyl, ethyl, propyl, butyl, and the like. If $R^4$ is hydrogen, the ortho-ester component is an ortho-formate component. If $R^4$ is methyl, the component is an ortho-acetate compound. An oligomeric or polymeric component containing the above ortho-ester moiety (5) can also be suitably used as neutralizing agent in the present invention.

The ortho-ester component generally has a Mw of at least 106, preferably, at least about 118, more preferred, at least about 200. The Mw of the ortho-ester component is preferably less than about 10,000 more preferably, less than about 8,000. Examples of an ortho-ester component are trialkyl ortho formate, such as trimethyl ortho formate, and trialkyl ortho acetates, such as trimethyl ortho acetate.

As the alcohol neutralizing component, well-known mono alcohols can be used, such as methanol, ethanol, and the like; alkoxylated alkyl-substituted phenol derivatives, such as ethoxylated and propoxylated nonylphenol, alkoxylated unsubstituted phenol derivatives, isodecylalcohol, laurylalcohol, isobornylalcohol, and the like.

Further, a wide range of well-known polyalcohols, preferably diols, can be used as the alcohol neutralizing component. Suitable polyalcohols comprise 2–10 alcohol groups, preferably 2–4 alcohol groups. Suitable examples include 1,3-propanediol, 1,3-butanediol, 1,4-butanediol, 1,5-pentanediol, 1,6-hexanediol, 1,9-nonanediol, diethylene glycol, triethylene glycol, tetraethylene glycol, polyethylene glycol, dipropylene glycol, polypropylene glycol, glycerol, trimethylol ethane, trimethylol propane (TMP), neopentyl glycol (NPG), pentaerythritol (PET), dipentaerythritol, sorbitol, 2-methyl-1,3-propane diol, 2,2-dimethyl-1,3-propanediol, 2-ethyl-1,3-propanediol, 2,2-diethyl-1,3-propanediol, 2-propyl-2-methyl-1,3-propanediol, 2-propyl-2-ethyl-1,3-propanediol, 2-butyl-2-ethyl-1,3-propanediol (BEPD), hydroxy pivaloyl hydroxy pivalate (HPHP), 2-cyclohexyl-2-methyl-1,3-propanediol, 2-phenyl-2-methyl-1,3-propanediol, 1,4-cyclohexanediol, 2,4-diethyl-1,5-pentane diol, or alkoxylated derivatives of all the above polyalcohols, such as preferably, ethoxylated and propoxylated derivatives thereof, ethoxylated bisphenol-A, propoxylated bisphenol-A, reduced dimer acid, and monoesters of the above, and the like. Reduced dimer acids are the hydrogenated analogs of dimer acids as described below. These diol components can be used in admixture.

Preferred alcohols as neutralizing agents are diols having the second hydroxy group in the γ-position, particularly preferred are 1,3-diols, neopentyl glycol (NPG), 2-butyl-2-ethyl-1,3-propane diol (BEPD), trimethylolpropane (TMP), pentaerythritol (PET), monoesters therefrom, or any mixture thereof.

Other preferred alcohols as neutralizing agent are monoesters of diols, preferably diols having a second hydroxy in the β- or γ-position towards the first hydroxy. If an alcohol is used as the neutralizing component, it is possible to catalyze said neutralizing step, for example, by adding neutralizing catalysts such as the components disclosed in Boyapati M. Choudary, Tetrahedron 56 (2000) 7291–7298.

Preferably, if only one component reacts with free acid groups, said component that reacts with the catalyst is not an epoxide, an amine, or carbodiimide component as such. Nevertheless, mixtures of a neutralizing component according to the present invention with an epoxide or amine component are suitable as well.

During the neutralizing step, the acid value of the resin is preferably being reduced to achieve a value of about 20 mg KOH/g or less, preferably about 15 mg KOH/g or less, more preferred about 10 mg KOH/g or less, particularly preferred about 5 mg KOH/g or less, and most preferred the resin is completely neutralized (acid value<0.1 mg KOH/g resin). Resins having a low acid value show improved hydrolytic stability.

The present invention further distinguishes between the acid value of the acidic catalyst (AV1) and the acid value of the remaining acid excluding the acidic catalyst (AV2).

The acid value of the acidic catalyst can be defined as "the acid value of strong acid", further defined as AV1, and is a measure for the amount of free catalyst acid remaining in the resin after the (meth)acrylation step. The acid value of the acidic catalyst, AV1, is expressed as the number of milligrams of potassium hydroxide that is required to neutralize the free acidic catalyst in one gram of the resin. According to the present invention, strong acid can be defined as acid having a pKa value of about 2 or less, determined at 25° C. in water.

The acid value of the remaining free acid excluding the acidic catalyst can be defined as "the acid value of weak (carboxylic) acid", further defined as AV2, and is a measure for the free carboxylic acids and remaining (meth)acrylic acids content in the resin. The acid value AV2 is expressed as the number of milligrams of potassium hydroxide required to neutralize the free carboxylic acids in one gram of the resin. According to the present invention weak acid is defined as acid having a pKa of more than about 2.

The neutralizing system (preferably the neutralizing component according to the present invention, more preferred the oxetane, ortho-ester, alcohol component, or any mixture thereof) is preferably added in an amount appropriate to obtain an AV1-value, of less than about 5 mg KOH/g of resin, more preferred, in an amount appropriate to obtain AV1 of less than about 3 mg KOH/g of resin, even more preferred in an amount appropriate to obtain AV1 of less than about 2 mg KOH/g of resin, particularly preferred, less than about 1 mg KOH/g of resin, even more preferred less than about 0.5 mg KOH/g of resin, and most preferred, between about 0 and about 0.1 mg KOH/g of resin.

Preferably, at least 10% of the acidic catalyst is being neutralized, more preferably, at least 20%, particularly preferred, at least 30%, even more preferred, at least, 50%, and most preferred, the catalyst is substantially completely reacted away.

It is more preferred to use the neutralizing component in such an amount that the amount of acidic catalyst as used in the synthesis is fully neutralized, preferably by using a small excess of neutralizing component compared to the amount of acidic catalyst as added in the synthesis.

The ester or amid compound formed between the catalyst and the neutralizing component according to the present invention in the ester of (meth)acrylic acid resin is a hydrolytically stable compound when stored in an open jar in an oven at 80° C. Preferably, the AV1 value of the (meth)acrylic acid ester resin does not increase, when stored in an open jar in an oven at 80° C. for at least 1 day, preferably, at least 2 days, more preferred, at least 4 days, particularly preferred, at least 1 week, and most preferred, at least 8 weeks. For example, when the catalyst is completely reacted away by the reaction with the neutralizing component of the present invention, the initial AV1=0 and this AV1-value remains equal to 0 for the time periods as specified above.

The neutralizing system (preferably, the oxetane, ortho-ester, alcohol component or any mixture thereof,) is preferably added in an amount appropriate to obtain a value for AV2 of less than about 20 mg KOH/g of resin, more preferred, in an amount appropriate to obtain an AV2 of less than about 15 mg KOH/g of resin, particularly preferred, less than about 5 mg KOH/g of resin, even more preferred between about 1–5 mg KOH/g of resin, and most preferred, between about 0–1 mg KOH/g of resin.

The neutralizing system (preferably the neutralizing component) is preferably added in an amount of about 300 mol % or less relative to the total mol % of acid groups in the resin, more preferably, about 200 mol % or less, even more preferred, about 150 mol % or less, particularly preferred, about 120 mol % or less. Relative to the total mol % of acid catalyst in the resin, the oxetane or ortho-ester component is preferably added in an amount of about 150 mol % or less, more preferably, about 120 mol % or less, particularly preferred, about 105 mol % or less.

It is more preferred to use the neutralizing system (preferably the neutralizing component) in such an amount that the total acid value (AV1+AV2) is <0.1 mg KOH/g resin, or preferably substantially equal to zero. It is even more preferred to use the neutralizing component in such an amount that besides the fact that the amount of acidic catalyst as used in the synthesis is fully neutralized, the AV2 value is substantially zero as well.

According to one preferred embodiment, the neutralizing component of the present invention or a mixture thereof reacts predominantly with strong acid having a pKa value of about 2 or less, including the catalyst acid. The weak acid having a pKa-value of more than about 2 is then neutralized by using the same or another neutralizing component (or mixture) according to the present invention, or by using a β-hydroxy forming component (for example an epoxide, such as glycidyl methacrylate, cyclohexene oxide, bisphenol-A-epoxides, and the like), an amine (such as dimethyl amino ethyl acrylate, dimethyl amino propyl acrylate, and the like), a carbodiimide or any mixture thereof.

More preferred, after the strong acid has been neutralized with the neutralizing component of the present invention, the weak acid is further reacted with a β-hydroxy forming component (such as an epoxide), an amine, or a carbodiimide since these components are relatively cheap. Another preferred option is to initially add as the neutralizing system at least one of the neutralizing components of the present invention (preferably, the oxetane, ortho-ester or alcohol component) in a mixture with an epoxide or amine component, preferably in a mixture with an epoxide component.

Optionally, any acid remaining after the neutralizing step according to the present invention can further be removed by different methods, such as by washing out, for example with aqueous base, extraction, distillation, further neutralization, or complexation with solid base. It is preferred to remove any remaining solvent and/or any remaining (carboxylic) acids by vacuum distillation under air purge. Said vacuum distillation is preferably carried out at temperatures in the range of about 100–180° C., more preferred in the range of about 120–160° C., even more preferred in the range of about 130–150° C. Further, said vacuum distillation is preferably carried out at pressures of less than about 0.5 bar, more preferred less than about 0.1 bar, even more preferred less than about 0.01 bar, particularly preferred around 10 mbar and preferably takes place, between about 15 minutes to about 5 hours, more preferred between about 30 minutes to about 4 hours, even more preferred between about 1 to 3 hours.

DETAILED DESCRIPTION OF THE SYNTHESIS PROCESS (Meth)acrylic ester monomers and polymers can be prepared and neutralized according to the process of the present invention.

In the preparation of the (meth)acrylic ester monomers a wide rang of well-known mono alcohols (i) can be used, such as methanol, ethanol, and the like; alkoxylated alkyl-substituted phenol derivatives, such as ethoxylated and propoxylated nonylphenol, alkoxylated unsubstituted phenol derivatives, isodecylalcohol, laurylalcohol, isobornylalcohol, monoesters of ethyleneglycol, monoesters of diols having the second hydroxy group in β- or γ-position towards the first hydroxy group, for example 1,2-diols, such as for example 1,2-propanediol, 1,2-butanediol, 2,3-butanediol, 2,3-pentanediol and monoesters of 1,3-diols, and the like.

Further, a wide range of well-known polyalcohols, preferably diols, can be used as the alcohol (i). Suitable polyalcohols comprise 2–10 alcohol groups, preferably 2–4 alcohol groups. Suitable examples include 1,2-propanediol, 1,3-propanediol, 1,2-butanediol, 1,3-butanediol, 1,4-butanediol, 1,5-pentanediol, 1,6-hexanediol, 1,9-nonanediol, ethylene glycol, diethylene glycol, triethylene glycol, tetraethylene glycol, polyethylene glycol, dipropylene glycol, polypropylene glycol, glycerol, trimethylol ethane, trimethylol propane, neopentyl glycol, pentaerythritol, dipentaerythritol, sorbitol, 2-methyl-1,3-propane diol, 2,2-dimethyl-1,3-propanediol, 2-ethyl-1,3-propanediol, 2,2-diethyl-1,3-propanediol, 2-propyl-2-methyl-1,3-propanediol, 2-propyl-2-ethyl-1,3-propanediol, 2-butyl-2-ethyl-1,3-propanediol (BEPD), hydroxy pivaloyl hydroxy pivalate (HPHP), 2-cyclohexyl-2-methyl-1,3-propanediol, 2-phenyl-2-methyl-1,3-propanediol, 1,4-cyclohexanediol, 2,4-diethyl-1,5-pentane diol, or alkoxylated derivatives of all the above polyalcohols, such as preferably, ethoxylated and propoxylated derivatives thereof, ethoxylated bisphenol-A, propoxylated bisphenol-A, reduced dimer acid, and the like. Reduced dimer acids are the hydrogenated analogs of dimer acids as described below. These diol components can be used in admixture.

Preferred are ethoxylated bisphenol-A, propoxylated bisphenol-A, neopentyl glycol (NPG), 2-butyl-2-ethyl-1,3-propane diol (BEPD), 2-methyl-1,3-propanediol (MPD), hydroxy pivaloyl hydroxy pivalate (HPHP), hydrogenated analogs of dimer acids, 2,4-diethyl-1,5-pentane diol or mixtures thereof. Particularly preferred are NPG, BEPD, and 2,4-diethyl-1,5-pentane diol, because the (meth)acrylic acid esters based on these alcohols show remarkably good hydrolytic stability. It is particularly preferred to use alcohols of which the β-position with respect to the hydroxyl group is substituted, more preferably, alcohols that have no hydrogen on the β-position.

The synthesis is generally carried out in a one-step process in which the alcohol compound (i), the (meth) acrylic acid (ii) and the catalyst are all charged in a reactor in air. The reaction can be carried out at a temperature ranging from about 80 to 150° C., preferably, about 100 to 140° C., more preferably about 120 to 130° C., at atmospheric or reduced pressure. If a solvent is present, the solvent preferably is toluene, heptane, xylene, benzene or the like, more preferably, toluene. The water is then removed azeotropically. The end of the reaction is followed by monitoring the acid value (as described above) or the hydroxyl value. The hydroxyl value is a measure of the amount of hydroxyl groups, and is measured by titrating back the reaction product of the polyester with acetic anhydride, and is expressed as given by formula (6):

$$\text{Hydroxyl value} = \frac{\text{the number of mg of potassium hydroxide (KOH)}}{\text{mass of resin or polymer (g)}} \quad (6)$$

The reaction can also be monitored by NMR. The reaction time generally is between about 1 to 24 hours, preferably, between about 1 to 16 hours, more preferred, between about 2 to 13 hours, and particularly preferred, between about 5 to 12 hours. If a solvent is present, it is preferably vacuum distilled together with any unreacted (meth)acrylic acid.

The (meth)acrylation reaction is preferably carried out until the hydroxyl conversion, as followed by NMR analysis, is completed for more than about 50%, more preferably, more than about 60%, particularly preferred, more than about 70%, and most preferred, more than about 95%. If reactants having relatively high functionality are used, only a lower hydroxyl conversion is required.

To inhibit polymerization of the acrylic double bonds, an inhibition system can be added. Examples of suitable inhibition systems are hydroquinone, derivatives of hydroquinone, such as methylether hydroquinone, 2,5-dibutyl hydroquinone (DBH), and the like, benzoquinone, derivatives of benzoquinone, such as methylether benzoquinone, 2,5-dibutyl benzoquinone and the like, nitrobenzenes, nitrostyrene, phenothiazines, and the like, copper (II) salts, such as Cu(II) naphthanate, and the like. Of these, 2,5-dibutyl hydroquinone (DBH) is preferred since a relatively low discoloration of the final oligomer can be achieved.

Stabilizers can further be used in the process, in particular color stabilizers, such as, for example, trisnonyl phenol phosphite (TNPP), trisphenol phosphite (TPP), bis-(2,4-di-t-butyl-phenyl)pentaerithritol-di-phosphite, and the like.

In the preparation of the (meth)acrylic ester polymers of the present invention, preferred polyalcohols (i) are polyether-based alcohols, such as polyethylene glycol (PEG), polypropylene glycol (PPG), polytetramethylene glycol (PTMG), a copolymer of PTMG and methyl-substituted PTMG (PTGL), a copolymer of ethyleneoxide and butyleneoxide, and the like; polyester-based alcohols, hydrocarbon-based alcohols; and the like. The hydrocarbon-based alcohols can comprise a linear or branched hydrocarbon containing a plurality of hydroxyl end groups. By "hydrocarbon" is meant a non-aromatic compound containing a majority of methylene groups and which may contain internal unsaturation and/or pendant unsaturation. Fully saturated (i.e. hydrogenated) hydrocarbons are preferred. Suitable hydrocarbon polyols include but are not limited to hydroxyl-terminated, fully or partially hydrogenated 1,2-polybutadiene polyol, 1,2-polybutadiene polyol hydrogenated to an iodine number of from 9 to 21; fully or partially hydrogenated polyisobutylene polyol, polybutene polyol, hydrogenated dimer diols, mixtures thereof, and the like. Preferably, the hydrocarbon polyol is substantially fully hydrogenated, and thus a preferred polyol is hydrogenated 1,2-polybutadiene.

The process of the present invention can advantageously be used in the synthesis of polymeric esters of (meth)acrylic acid because a washing step of high viscous components is difficult whereas the neutralizing step of the present invention is advantageous, more preferred in the synthesis of polyester (meth)acrylates. The neutralization process of the present invention is found to be advantageous in preparing end standing diacrylates. A further advantage is that the catalyst used in the preparation of the polyester polyol can be further used in the subsequent acrylation step and thus, does not need to be washed away.

Polyester acrylates having a relatively low amount of ester linkages are preferred. Also preferred are hydrophobic polyester acrylates. To obtain more hydrolytically resistant polyester acrylates, its building blocks can be modified, for example by choosing more hydrolytically stable and/or more sterically hindered polybasic acid and/or alcohol building blocks. Polyester acrylates having reduced acid values can be chosen as well.

The polyester backbone according to the invention is derived from (i) polyalcohols and (ii) saturated or unsaturated polybasic acids to obtain polyester polyols. Saturated polybasic acids and polyalcohols are preferred. The polyester polyol is then further reacted with (iii) acrylic or methacrylic acid to obtain the polyester (meth)acrylate.

A preferred polyester acrylate contains between about 0.5 and 20 diacids, more preferred between about 1 and about 5, particularly preferred, between about 2 and about 4, and most preferred, at least about 2.5.

In case the polyester is an alkyd, the alkyd can be made by any method. Preferably, alkyd resins can be prepared by condensation reactions of polyfunctional alcohols (hereafter referred to as polyols), polyfunctional carboxylic acids (hereafter referred to as polyacids), and oils or fatty acids derived from the oils. The oil can be a natural oil (which consists of an ester, e.g., a triester of glycerol and fatty acids). For example, a polyol/fatty acid mixture can be prepared in situ by alcoholysis of a naturally derived oil or by direct esterification of a polyol with a naturally derived long chain fatty acid. The resulting product from either of these reactions can then be polymerized with other polyols and polyacids (e.g., diols and diacids) as in conventional polyesterification. More preferably, the alkyd is prepared by alcoholysis of a naturally derived oil, preferably one with a low degree of unsaturation.

(i) As the polyalcohol, a wide range of well-known polyalcohols can be used, as listed above under the preparation of the (meth)acrylic ester monomers.

(ii) As the polybasic acids for the polyester and/or alkyd acrylates, polyfunctional carboxylic acids and the corresponding anhydrides can be used. Preferably, aromatic or aliphatic dibasic carboxylic acids and the corresponding anhydrides are used such as phthalic acid or anhydride, isophthalic acid, terephthalic acid, maleic acid or anhydride, fumaric acid, itaconic acid or anhydride, adipic acid, glutaric acid, azelaic acid, sebacic acid, citric acid, trimellitic acid or anhydride, pyromellitic acid or dianhydride, dodecane dicarboxylic acid, dodecane dioic acid, cyclohexane dicarboxylic acid, tetrahydrophthalic acid anhydride, methylene tetrahydrophthalic acid or anhydride, hexahydrophthalic acid anhydride, succinic acid or acid anhydrides thereof or lower alkyl esters thereof, dimer-fatty acid and the like. Mixtures of acids may also be used.

Dimer acids (and esters thereof) are a well known commercially available class of dicarboxylic acids (or esters). They are normally prepared by dimerizing unsaturated long chain aliphatic monocarboxylic acids, usually of 13 to 22 carbon atoms, or their esters (e.g. alkyl esters). The dimerization is thought by those in the art to proceed by possible mechanisms, said mechanisms including Diels-Alder, free radical, and carbonium ion mechanisms. The dimer acid material will usually contain 26 to 44 carbon atoms. Particularly, examples include dimer acids (or esters) derived from C-18 and C-22 unsaturated monocarboxylic acids (or esters) that will yield, respectively, C-36 and C-44 dimer acids (or esters). Dimer acids derived from C-18 unsaturated acids, which include acids such as linoleic and linolenic are particularly well known (yielding C-36 dimer acids).

The dimer acid products will normally also contain a proportion of trimer acids (e.g. C-54 acids when using C-18 starting acids), possibly even higher oligomers and also small amounts of the monomer acids. Several different grades of dimer acids are available from commercial sources and these differ from each other primarily in the amount of monobasic and trimer acid fractions and the degree of unsaturation.

Usually the dimer acid (or ester) products as initially formed are unsaturated which could possibly be detrimental to their oxidative stability by providing sites for crosslinking or degradation, and so resulting in changes in the physical properties of the coating films with time. It is therefore preferable (although not essential) to use dimer acid products that have been hydrogenated to remove a substantial proportion of the unreacted double bonds.

Herein the term "dimer acid" is used to collectively convey both the diacid material itself or to ester-forming derivatives thereof (such as lower alkyl esters) which would act as an acid component in polyester synthesis, and includes (if present) any trimer or monomer.

Particularly preferred are adipic acid, isophthalic acid, terephthalic acid, and dimer-fatty acid or mixtures thereof. Also preferred are tetrahydrophthalic acid anhydride, hexahydrophthalic acid anhydride, 1,4-cyclohexane dicarboxylic acid (CHDA), succinic acid or mixtures thereof. Polyester acrylates based on these acids generally show good hydrolytic stability.

For the alkyds, the monoacid can be any monocarboxylic acid having between 4 and 28 carbon atoms. Preferably, the monoacid is a fatty acid, more preferably a long chain monoacid. A long chain monoacid, or long chain fatty acid, is characterized as having between 12 and 28 carbon atoms in their chain; more preferably, between 12 and 24 carbon atoms. Most fatty acids have 18 carbon atoms in their chain, but also a higher number of carbon atoms in naturally derived oils is possible. For example, $C_{22}$ acid, erucic acid (docosenoic acid), is found in some varieties of rapeseed oil. Preferably, naturally derived fatty acids or oils from which fatty acids are derived, as known to those skilled in the art, are fatty acids or oils originating from vegetable or animal sources.

The fatty acids or oils suitable in the alkyd backbones according to the present invention can be unsaturated or saturated. Preferably, the fatty acids or oils have a low degree of unsaturation, as defined hereunder. Examples of unsaturated oils or fatty acids (derived from the oils) include castor oil, corn oil, cottonseed oil, rapeseed oil, low eruric rapeseed oil, hempseed oil, kapok oil, linseed oil, wild mustard, oiticica oil, olive oil, palm oil, peanut oil, peerilla oil, poppyseed oil, tobaccoseed oil, argentine rapeseed oil, rubberseed oil, safflower oil, sesame oil, soybean oil, sugarcane oil, sunflower oil, tall oil, teaseed oil, tung oil, black walnut oil, or mixtures thereof, and the like.

Examples of fatty acids/oils having a low degree of unsaturation include coconut oil, babassu oil, Chinese tallow oil, ouri-curl oil, palm kernel oil, caprylic acid, caproic acid, capric acid, coconut fatty acid, lauric acid, myristic acid, palmitic acid, stearic acid, and the like or mixtures thereof, fatty acids derived from the oils, as well as the hydrogenated form of unsaturated oils and fatty acids derived from the oils, such as castor oil, corn oil, cottonseed oil, rapeseed oil, low eruric rapeseed oil, hempseed oil, kapok oil, linseed oil, wild mustard, oiticica oil, olive oil, palm oil, peanut oil, perilla oil, poppyseed oil, tobaccoseed oil, argentine rapeseed oil, rubberseed oil, safflower oil, sesame oil, soybean oil, sugarcane oil, sunflower oil, tall oil, teaseed oil, tung oil, black walnut oil, or mixtures thereof, and the like.

(iii) The (meth)acrylation of the (poly)ester polyol is finally carried out with (meth)acrylic acid or their lower alkyl esters as defined by formula (1). The lower alkyl esters preferably have 1–6 carbon atoms.

The polymeric (trans)esterification, and in particular for the preparation of the polyester (meth)acrylates, ca be carried out in a one-step, two-step or more-step process.

In the one-step process, the alcohol component (i), the acid component (ii), (meth)acrylic acid (iii) and catalyst are all charged in a reactor in air and the same reaction conditions apply as for the monomeric esterification described above.

According to a preferred embodiment of the present invention the (poly)ester (meth)acrylate is prepared according to a two-steps synthesis process, in particular in case of bad solubility of one of the components, e.g. one of the acids. During step 1 of the two-steps process, the (poly)ester polyol is prepared by esterification of the acid (ii) and the alcohol (i) components at a temperature in the range of about 150–250° C., preferably 160–240° C., more preferred 180–230° C., preferably under nitrogen atmosphere. A solvent may also be present as discussed above. Preferably, the reaction is carried out under pressure, more preferably, at a pressure of about 10 bar or less, particularly preferred, at a pressure of about 6 bar or less and more preferred at a pressure of 2 bar or less. Generally, excess alcohol component is used in comparison with acid component to yield hydroxyl functional compounds.

As an (trans)esterification catalyst in step 1, organic acid, inorganic acid and metal catalysts are effective. Of these, organic acid catalysts and metal catalysts are preferred because of a high purity of the product and their effectiveness as a catalyst. As organic acid catalysts, alkyl sulfonic acids such as methane sulfonic acid, aryl sulfonic acids, such as p-toluene sulfonic acid and benzene sulfonic acid, and the like can be given. As inorganic catalyst, sulfuric acid, phosphoric acid, and the like can be given. As metal catalysts, tetra-isopropyl titanate, tetra-phenyl titanate, hydroxy titanium stearate, tetra-stearyl titanate, tetraethyl zirconate, tetra butoxy titannate ($(BuO)_4Ti$), dibutyl tin oxide ($Bu_2$-SnO), butyl stannic acid (BuSnOOH), butyl tin chloro dihydroxide ($BuSnCl(OH)_2$)), and the like can be given. P-toluene sulfonic acid is particularly preferred because it is a highly effective catalyst and because of it's low cost. Particularly preferred are further butyl stannic acid and butyl tin chloro dihydroxide since only a small amount of the catalyst is needed to achieve a relatively high reactivity, in particular at the high temperatures of the first step reaction.

Step 2 of the two-steps process, the (meth)acrylation of the (poly)ester diol of step 1 takes place under the same reaction conditions, such as temperature and reaction time, as described for the one-step process above. The reaction is preferably carried out (with air purge) by the addition of (meth)acrylic acid in a solvent, such as toluene, in the presence of a catalyst and an inhibition system to stabilize the acrylic unsaturation.

The Mn of the polyester polyol generally lies between about 400 and about 14,500, preferably, between about 500 and about 10,000, more preferably, between about 600 and about 9,000.

The OH-functionality of the polyester backbone in general will be lower than about 5, more preferably lower than about 3. The functionality of the polyester backbone in general will be at least about 1.5, preferably, at least about 1.8. Preferably, the functionality is between about 2.0 and 2.5.

The esters of (meth)acrylic acid prepared according to the process of the present invention can be solid or liquid, and can be used in a wide range of applications.

One field of application for example is in coatings, either wet, water-based or solid (so-called powder) coatings. The wet coatings can be divided in solvent-based and 0% VOC (volatile organic compound) systems. With 0% VOC system is meant a system that does not contain a solvent; in some cases a very low amount of volatiles can escape during the curing reaction of the solid components.

All of these coatings can be applied on untreated or pre-coated wood, wood-like substrates, glass, metal, plastic and hybrid surfaces. Examples of wood-like materials are for example plywood, chipwood and MDF (medium density fiber board). With hybrid surfaces are surfaces meant that comprise different materials, for example combinations of metal and wood.

The curing mechanism of the coating composition is not particularly critical. It can be cured thermally or by radiation curing. It is preferred to use these esters of (meth)acrylic acid in a coating composition that can be cured by UV-radiation. When UV-radiation is applied it is preferred to use UV-initiated curing in the presence of photoinitiators, for example Norrish type 1 and 2 photoinitiators. When a thermal cure is applied it is preferred to use a radically initiated curing in the presence of peroxides (either alone or in combination with accelerators), for example azo-isobutylnitrile (AIBN) and cobalt-compounds.

The esters of (meth)acrylic acid can be used in a coating composition as sole binder but also in combination with binders based on the same or different technology.

In powder coatings, for instance, it is possible to mix a crystalline and/or semi-crystalline ester of (meth)acrylic acid with an amorphous ester of (meth)acrylic acid to obtain good flow in combination with a good powder stability and good processing characteristics. It is also possible to combine a crystalline and/or semi-crystalline ester of (meth) acrylic acid with completely different binders, like amorphous GMA-functionalized polyesters as described in patent WO 98/18862.

In solvent and/or 0% VOC systems the esters of (meth) acrylic acid can also be used in a coating composition as sole binder but also in combination with other oligomers, reactive diluents and solvents.

In water-based systems the ester of (meth)acrylic, acid can be dispersed or emulsified in water by use of standard techniques as described in Emulsion Polymerisation, Theory and Practice, Ed. D. C. Blackley, Applied Science Publishers, London 1975, ISBN: 0 85334 627 5.

Other fields of application of the esters of (meth)acrylic acid are in reactive hot melt adhesives, in sizings and binder resins, dental applications, contact lenses, optical disk adhesives (for example for DVD, CD or CD-R), hardcoats and stereolithography. The esters of (meth)acrylic acid also may be used in composite resin compositions, for instance for sheet molding compounding (SMC) resins, castings resins, pultrusion resins, low or zero content styrene resins, hand lay-up resin transfer molding, prepregs, etc., such as for instance can be used for the preparation of molded parts, structural elements, glass fiber laminates, and the like.

Description of Test Methods
Method for Measuring the Acid Value AV

About 2 gram of sample is diluted in 25 ml THF. Then 1 ml water is added to dissociate the acid(s) into its (their) ions. The mixture is potentiometrically titrated with 0.1M potassium hydroxide in methanol standard solution (KOH/MeOH) after it is stirred for 5 minutes. Both acid values (AV1, for acids having a $pKa \leq 2$, and AV2, for acids having a $pKa > 2$) are automatically determined on a Toledo DL58 Titrator.

Further, in order to more accurately determine the strong acid value AV1, the amount of sample can be increased. The appropriate amount of sample depends on the expected acid value. Some guidelines are:
- AV<1: amount sample>2 gram
- 1<AV<100: amount sample 0.5–2 gram
- AV>100: amount sample:<0.5 gram The acid value is automatically calculated on the basis of the formulation (7):

$$AV = (V_{eq.} * t * 56.1) / m \quad (7)$$

where: AV=Acid Value
$V_{eq}$=volume (ml) titrant used in equivalence point
t=titer of 0.1 n KOH
m=amount of sample in gram

EXAMPLES AND COMPARATIVE EXPERIMENTS

Examples 1–3
Synthesis of (meth)acrylate Monomers

Example 1
Synthesis of Phenoxyethyl Methacrylate

Phenoxyethanol was mixed with 105 mol % methacrylic acid and next 30% toluene, 1% PTSA, 0.1% dibutylhydroquinon (all based on amount alcohol+methacrylic acid) were added. Air was purged through the reaction mixture and the temperature was increased till boiling toluene. Next the mixture was refluxed (120–130° C.) for 8 hours in a flask equipped with a Dean-Stark set up to remove the reaction water.

After 8 hours a sample was taken and titrated potentiometrically to determine the acid value belonging to free PTSA (AV1) and the acid value of the carboxylic acids (AV2). Next 105 mol % (to AV1 of PTSA) 3-ethyl-3-hydroxymethyl-oxetane was added to neutralise the PTSA. After 15 min a sample was taken to check if the AV1=0 and subsequently the solvent and residual methacrylic acid were removed via a distillation at 130° C. and 50 mm Hg. The final values were AV1=0 and AV2=16.4.

Example 2
Synthesis of Ethoxylated (2 Times on Average) Bisphenol A Dimethacrylate Ethoxylated (2 times on average) bisphenol A dimethacrylate was made in the same way as example 1, but starting from ethoxylated bisphenol A instead of phenoxyethanol and the inhibition system was extended with 8 ppm Cu(II) naphthenate. The final values were AV1=0 and AV2=2.5.

Example 3
Synthesis of Trimethylol Propane Trimethacrylate

Trimethylol propane trimethacrylate was made in the same way as example 1, but instead of phenoxyethanol, trimethylol propane was used as the starting material. The final values were AV1=0 and AV2=2.8.

Examples 4–5
Synthesis of Polyether (meth)acrylates

Example 4
Synthesis of Polytetrahydrofuran Diacrylate

Polytetrahydrofuran Mn=1000 was mixed with 105 mol % acrylic acid (to amount OH) and next 30% toluene, 1% PTSA, 0.1% dibutylhydroquinon (all based on amount alcohol+acrylic acid) were added. Air was purged through the reaction mixture and the temperature was increased till boiling toluene. Next the mixture was refluxed (120–130° C.) for 8 hours in a flask equipped with a Dean-Stark set up to remove the reaction water.

After 8 hours a sample was taken and titrated potentiometrically to determine the acid value belonging to free PTSA (AV1) and the acid value of the carboxylic acids (AV2). Next 105 mol % (to AV1 of PTSA) 3-ethyl-3-hydroxymethyl-oxetane was added to neutralise the PTSA. After 15 min a sample was taken to check if the AV1=0 and subsequently the solvent and residual acrylic acid was removed via a distillation at 130° C. and 50 mm Hg. The final values were AV1=0 and AV2=1.5.

Example 5
Synthesis of Polyethyleneglycol Dimethacrylate

Triethylene glycol was methacrylated in the same way as example 4 and the inhibition system was extended with 8 ppm Cu(II) naphthenate. The final values were AV1=0 and AV2=11.6.

Example 6
Synthesis of Liquid Polyester Acrylates I–IV:

The polyester acrylates I–IV are prepared according to the two-step synthesis process as described in the above specification. In step 1, isophthalic acid (IPA) is reacted with BEPD (2-butyl-2-ethyl-1,3-propanediol) in the presence of 0.2% (based on total amount of IPA and BEPD) of BuSnOOH as a catalyst. The end of step 1 is indicated when the acid value (AV) is below 5 and all IPA is dissolved. The general experimental conditions of step 2 are:

| | |
|---|---|
| amount acrylic acid (AA): | 105 mol % |
| amount toluene: | 35 wt. % (based on total amount of IPA + BEPD + AA) |
| amount PTSA: | 1 wt. % (based on IPA + BEPD + AA) |
| inhibition system: | 1000 ppm DBH, 1000 ppm TNPP, air purge (1 l/h/l) |
| reaction temperature: | 125–130° C. |
| reaction time: | 12–16 hours (till >95% OH conversion by NMR) |
| PTSA neutralisation: | reaction with 150 mol % of neutralizer |
| solvent distillation: | at 120° C. and 20 mbar (till the amount of toluene left is less than about 0.5%) |

The amounts of the reactants used in said process are given for each of the polyester acrylates I–IV:

Polyester acrylate I: 5 mol BEPD, 4 mol IPA and 2 mol AA, neutralized with 3-ethyl-3-hydroxymethyl-oxetane (UVR-6000), theoretical Mn=1428

Polyester acrylate II: 5 mol BEPD, 4 mol IPA and 2 mol AA, neutralized with trimethyl ortho formate, theoretical Mn=1428

Polyester acrylate III: 3.5 mol BEPD, 2.5 mol IPA and 2 mol AA, neutralized with 3-ethyl-3-hydroxymethyl-oxetane (UVR-6000), theoretical Mn=1020

Polyester acrylate IV: 6.5 mol BEPD, 5.5 mol IPA and 2 mol AA, neutralized with 3-ethyl-3-hydroxymethyl-oxetane (UVR-6000), theoretical Mn=1880.

Example 7
Synthesis of Liquid Alkyd Acrylate V:

The alkyd acrylate V is prepared according to a 3-step synthesis process. In the first step, 1 mol coconut fatty acid (Prifac7901 of Unichema) was reacted with 1 mol trimethylol propane (TMP) with BuSnOOH at 185° C. till the acid value is below 5. In the second step, the fatty acid diol was reacted with 3 mol neopentyl glycol (NPG), 2 mol IPA and 1 mol adipic acid (ADA) till the acid value was below 5 to make an alkyd polyol. In the last step, this polyol was acrylated with acrylic acid in refluxing toluene (130° C.) with 1% PTSA as catalyst. The OH-conversion was followed by NMR. After about 95% conversion, the PTSA was neutralised with 200% 3-ethyl-3-hydroxymethyl-oxetane (UVR-6000) (towards AV1 of PTSA) and the solvent was evaporated. Finally a yellow viscous resin was obtained (GPC Mn/Mw=1600/4800).

Examples 8–9 and Comparative Experiments 1–2

Synthesis and Neutralisation of Liquid Polyester Acrylate VI

Synthesis process:

Step 1, synthesis of polyester polyol: 1 mol isophthalic acid and 2 mol butylethylpropanediol (BEPD) were esterified with 0.1% $BuSnCl(OH)_2$ as a catalyst at 180–220° C. till the acid value.

Step 2, acrylation step: the polyester polyol of step 1 was cooled down to 100° C. and mixed with 105 mol % acrylic acid (to amount OH), 30% toluene, 1% PTSA and 0.1% dibutylhydroquinon DBH (all based on amount polyester polyol+acrylic acid). Air was purged through the reaction mixture and the temperature was increased till boiling toluene. Next, the mixture was refluxed (120–130° C.) for 8 hours in a flask equipped with a Dean-Stark set up to remove the reaction water. If necessary, the pressure was reduced to keep the toluene refluxing. After 8 hours a sample was taken and titrated potentiometrically to determine the acid value belonging to free PTSA (AV1) and the acid value of the carboxylic acids (AV2). AV1 was 2.5 and AV2 was 8.8. Next the liquid polyester acrylate resin VI was divided into 5 parts.

Neutralisation process:

Example 8

The resin was neutralised with 150 mol % (to AV1 of PTSA) 3-methyl-3-hydroxymethyl-oxetane. After 15 min a sample was taken to check if the AV1=0 and subsequently the solvent and residual acrylic acid was removed via a distillation at 130° C. and 50 mm Hg.

Example 9

The resin was neutralised with 150 mol % (to AV1 of PTSA) trimethyl ortho formate. After 15 min a sample was taken to check if the AV1=0 and subsequently the solvent and residual acrylic acid was removed via a distillation at 130° C. and 50 mm Hg.

Comparative Experiment 1

The resin was not neutralised, the solvent and residual acrylic acid were removed via a distillation at 130° C. and 50 mm Hg.

Comparative Experiment 2

The resin was neutralised with 150 mol % (to AV1 of PTSA) glycidyl methacrylate. After 15 min a sample was taken to check if the AV1=0 and subsequently the solvent and residual acrylic acid was removed via a distillation at 130° C. and 50 mm Hg.

To test the hydrolytic stability, 20 gram samples of the resins of examples 8–9 and Comparative Experiments 1–2 were stored in an open jar in an oven at 80° C. After several time intervals the strong acid value AV1 (=PTSA) and the weak acid value AV2 (=carboxylic acid) were measured.

As shown in Table 1, the samples neutralised with an oxetane (Ex. 8) or ortho ester (Ex. 9) do not show any strong acid (AV1=0) even after 8 weeks. This in contrast with the unneutralised sample (Comp. Exp. 1) and the glycidyl methacrylate neutralised sample (Comp. Exp. 2), which clearly show the presence of PTSA.

TABLE 1

Hydrolytic stability of liquid polyester acrylate-VI at 80° C.

| time at 80° C. | Ex. 8 3Me-3-hydroxy-Me-oxetane | | Ex. 9 trimethyl ortho formate | | Comp. Exp. 1 Unneutralised | | Comp. Exp. 2 Glycidyl methacrylate | |
|---|---|---|---|---|---|---|---|---|
| | $AV_1$ | $AV_2$ | $AV_1$ | $AV_2$ | $AV_1$ | $AV_2$ | $AV_1$ | $AV_2$ |
| 0 day | 0.0 | 8.7 | 0.0 | 12.1 | 2.5 | 8.8 | 0.0 | 8.6 |
| 1 day | 0.0 | 9.3 | 0.0 | 11.2 | 2.5 | 9.2 | 1.0 | 7.2 |
| 4 days | 0.0 | 9.0 | 0.0 | 9.7 | 2.6 | 10.3 | 1.7 | 8.1 |
| 1 week | 0.0 | 9.2 | 0.0 | 8.8 | 2.6 | 10.3 | 1.7 | 8.7 |
| 2 weeks | 0.0 | 9.0 | 0.0 | 7.7 | 2.4 | 8.4 | 2.0 | 7.6 |
| 5 weeks | 0.0 | 8.2 | 0.0 | 7.5 | 2.1 | 7.0 | 2.1 | 6.6 |
| 8 weeks | 0.0 | 7.9 | 0.0 | 8.2 | 2.3 | 6.6 | 2.0 | 7.1 |

Example 10–11

Synthesis and Neutralisation of Liquid Polyester Acrylate VII

Synthesis process:

Step 1, synthesis of polyester polyol: 3.5 mol isophthalic acid, 2 mol adipic acid and 6.5 mol butylethylpropanediol (BEPD) were esterified with 0.1% $BuSnCl(OH)_2$ at 180–220° C. till acid value is below 5.

Step 2, acrylation step: the polyester polyol of step 1 was cooled down to 100° C. and mixed with 105 mol % acrylic acid (to amount OH), 15% toluene, 1% PTSA and 0.1% dibutylhydroquinon (all based on amount polyester polyol+acrylic acid). Air was purged through the reaction mixture and the temperature was increased till boiling toluene. Next the mixture was refluxed (120–130° C.) for 8 hours in a flask equipped with a Dean-Stark set up to remove the reaction water. If necessary, the pressure was reduced to keep the toluene refluxing. After 8 hours a sample was taken and titrated potentiometrically to determine the acid value belonging to free PTSA (AV1) and the acid value of the carboxylic acids (AV2).

Neutralisation Process:

Example 10

Next, 105 mol % (to AV1 of PTSA) 3-ethyl-3-hydroxymethyl-oxetane was added to neutralise the PTSA. After 15 min a sample was taken to check if the AV1=0 and subsequently the solvent and residual acrylic acid was removed via a distillation at 130° C. and 50 mm Hg. The final values were AV1=0 and AV2=8.0.

Example 11

To neutralise the strong acid 300 mol % neopentyl glycol (relative to the amount added PTSA) was added. The reflux was continued till AV1 was zero. Subsequently the solvent and residual acrylic acid were removed via a distillation at 130° C. and 50 mm Hg. The final values were AV1=0 and AV2=3.0.

Example 12

Synthesis and Neutralisation of Liquid Polyester Acrylate VII

The synthesis process of Example 10 was repeated by using 0.5% $H_2SO_4$ instead of 1% PTSA as the catalyst in step 2. The final values were AV1=0 and AV2=9.0.

Example 13
Synthesis and Neutralisation of Liquid Polyester Methacrylate VIII Step 1, synthesis of polyester polyol: 1 mol phthalic anhydride, 1.8 mol triethylene glycol and 0.2 mol trimethylol propane were esterified with 1% PTSA at 180° C. till acid value is below 10. To enhance the water removal 3% toluene was added and a Dean-Stark set up was used.

Step 2, methacrylation step: the polyester polyol of step 1 was cooled down to 100° C. and mixed with 105 mol % methacrylic acid (to amount OH), 15% toluene, 1% PTSA and 0.1% dibutylhydroquinon (all based on amount polyester polyol+methacrylic acid). Air was purged through the reaction mixture and the temperature was increased till boiling toluene. Next, the mixture was refluxed (120–130° C.) for 8 hours in a flask equipped with a Dean-Stark set up. If necessary, the pressure was reduced to keep the toluene refluxing. After 8 hours a sample was taken and titrated potentiometrically to determine the acid value belonging to free PTSA (AV1) and the acid value of the carboxylic acids (AV2).

Next 105 mol % (based on added PTSA) 3-ethyl-3-hydroxymethyl-oxetane was added to neutralise the PTSA. After 15 min a sample was taken to check if the AV1=0 and subsequently the solvent and residual acrylic acid was removed via a distillation at 130° C. and 50 mm Hg. The final values were AV1=0 and AV2=12.0.

Example 14
Synthesis and Neutralisation of Solid Amorphous Polyester Acrylate IX Step 1, synthesis of polyester polyol: 20 mol terephthalic acid, 20 mol neopentyl glycol and 1 mol trimethylol propane were esterified with 0.1% BuSnCl(OH)$_2$ at 180–240° C. till acid value <10.

Step 2, acrylation step: the polyester polyol of step 1 was cooled down to 120° C. and mixed with 105 mol % acrylic acid (to amount OH), 15% toluene, 1% PTSA and 0.2% dibutylhydroquinon (all based on amount polyester polyol+acrylic acid). Air was purged through the reaction mixture and the temperature was increased till boiling toluene. Next, the mixture was refluxed (120–140° C.) for 8 hours in a flask equipped with a Dean-Stark set up. If necessary, the pressure was reduced to keep the toluene refluxing. After 8 hours a sample was taken and titrated potentiometrically to determine the acid value belonging to free PTSA (AV1) and the acid value of the carboxylic acids (AV2).

Next, 105 mol % (to AV1 of PTSA) 3-ethyl-3-hydroxymethyl-oxetane was added to neutralise the PTSA. After 15 min a sample was taken to check if the AV1=0 and subsequently the solvent and residual acrylic acid was removed via a distillation at 160° C. and 50 mm Hg. The final values were AV1=0 and AV2=8.9.

Example 15
Synthesis and Neutralisation of Solid Semi-Crystalline Polyester Acrylate X Step 1, synthesis of polyester polyol: 3.5 mol terephthalic acid, 4.5 mol hexane diol were esterified with 0.1% BuSnCl(OH)$_2$ at 180–240° C. till acid value is below 5.

Step 2, acrylation step: the polyester polyol of step 1 was cooled down to 100° C. and mixed with 105 mol % acrylic acid (to amount OH), 15% toluene, 1% PTSA and 0.2% dibutylhydroquinon (all based on amount polyester polyol+acrylic acid). Air was purged through the reaction mixture and the temperature was increased till boiling toluene. Next, the mixture was refluxed (120–140° C.) for 8 hours in a flask equipped with a Dean-Stark set up. If necessary, the pressure was reduced to keep the toluene refluxing. After 8 hours a sample was taken and titrated potentiometrically to determine the acid value belonging to free PTSA (AV1) and the acid value of the carboxylic acids (AV2).

Next, 105 mol % (to AV1 of PTSA) 3-ethyl-3-hydroxymethyl-oxetane was added to neutralise the PTSA. After 15 min a sample was taken to check if the AV1=0 and subsequently the solvent and residual acrylic acid was removed via a distillation at 160° C. and 50 mm Hg. The final values were AV1=0 and AV2=8.0.

What is claimed is:

1. Process for the preparation of esters of (meth)acrylic acid comprising (trans)esterifying (meth)acrylic acid or its ester derivatives with monohydric or polyhydric alcohols in the presence of an acidic (trans)esterification catalyst selected from the group consisting of sulfuric acid, monoester of sulfuric acid, phosphoric acid, monoester of phosphoric acid, para-toluene sulfonic acid, benzene sulfonic acid, styrene sulfonic acid and methane sulfonic acid, wherein said process after the formation of the esters of (meth)acrylic acid further comprises reacting free acid groups with a neutralizing system comprising one or more component(s), wherein at least one component is selected from the group consisting of an oxetane compound or derivative thereof, an ortho-ester compound, and an alcohol compound or a mixture of two or more of said compounds and forms with at least said acid (trans)esterification catalyst an ester compound not having a β-hydroxyl group or an amid compound, wherein the neutralizing system is used in an amount of about 300 mol % or less, relative to the total amount of acids.

2. Process according to claim 1, wherein said at least one component forms with at least said acidic (trans)esterification catalyst an ester compound not having a β-hydroxy compound.

3. Process according to claim 1, wherein when a β-hydroxy forming component, an amine component, a carbodiimide component or a mixture of two or more thereof is present, said component(s) are added only after the acidic catalyst has been neutralized with said at least one component that forms an ester compound not having a β-hydroxy group or forms an amid compound.

4. Process according to claim 1, wherein said at least one component additionally forms with the remaining free acid groups an ester compound not having a β-hydroxy group or forms an amid compound.

5. Process according to claim 1, wherein the remaining free acid groups comprise free (meth)acrylic acid groups and free carboxylic acid groups.

6. Process according to claim 1, wherein the at least one compound is selected from the group consisting of 3-ethyl-3-hydroxymethytl-Oxetane, 3-methyl-3-hydroxymethyl-oxetane, trialkyl ortho formate, trialkyl ortho acetate, and neopentylglycol.

7. Process according to claim 1, wherein a said neutralizing system is added in on amount appropriate to obtain an acid value of the free acid excluding the acidic catalyst, AV1 of less than about 2 mg KOH/g of resin.

8. Process according to claim 1, wherein a said neutralizing system is added in an amount appropriate to obtain an acid value of the free acid excluding the acidic catalyst, AV2. of less than about 20 mg KOH/g of resin.

9. Process according to claim 1, wherein said neutralizing system further comprises one or more compounds selected from the group consisting of a β-hydroxy forming compound, an amine compound, and a carbodiimide compound.

10. Process according to claim 1, wherein the neutralizing system is added in an amount of about 200 mol % or less relative to the total amount of acids.

11. Process according to claim 1, wherein the at least one component is added in an amount of 105 mol % or more relative to the total mol % of acid catalyst.

12. Process according to claim 1, wherein the ester of (meth)acrylic acid is a (meth)acrylate functional polyester or polyalkyd.

13. Ester of (meth)acrylic acid resin obtained by the process of claim 1, wherein the acid value of the resin does not substantially increase when stored in an open jar I an oven at 80° C. for at least 1 day.

14. Ester of (meth)acrylic acid resin according to claim 13, wherein the AV1 value of said resin is less than about 5 mg KOH/g of resin.

15. Powder coating composition comprising an ester of (meth)acrylic acid obtained according to the process of claim 1 and a photoinitiator or a peroxide.

16. Powder coating composition according to claim 15, wherein the composition comprises a mixture of a crystalline and/or semi-crystalline ester of (meth)acrylic acid with an amorphous ester of (meth)acrylic acid.

17. Powder coating composition according to claim 15, wherein the composition contains a photoinitiator and is UV-curable.

18. Wet coating composition comprising an ester of (meth)acrylic acid obtained according to the process of claim 1 and a photoinitiator or a reactive diluent.

19. Composite resin comprising an ester of (meth)acrylic acid obtained according to the process of claim 1 and a peroxide or a reactive diluent.

20. Process according to claim 1, wherein said at least one component is added to said product composition in amount of 150 mol % or less relative to the total mol % of said catalyst.

21. Process according to claim 1, wherein said catalyst is selected from the group consisting of para-toluene sulfonic acid, benzene sulfonic acid, styrene sulfonic acid and methane sulfonic acid.

* * * * *